(12) United States Patent
Panzeri

(10) Patent No.: US 7,235,639 B2
(45) Date of Patent: Jun. 26, 2007

(54) HEMOGLOBIN CONJUGATES

(76) Inventor: Ezio Panzeri, Via Sapri 11, Milano (IT) 20156

( * ) Notice: Subject to any disclaimer, the term of this patent is extended or adjusted under 35 U.S.C. 154(b) by 244 days.

(21) Appl. No.: 10/420,966

(22) Filed: Apr. 23, 2003

(65) Prior Publication Data

US 2004/0214748 A1    Oct. 28, 2004

(51) Int. Cl.
*C07K 14/00* (2006.01)
*A61K 35/14* (2006.01)
*A61K 38/00* (2006.01)

(52) U.S. Cl. .................. 530/385; 530/350; 530/402; 514/385

(58) Field of Classification Search .................. None
See application file for complete search history.

(56) References Cited

U.S. PATENT DOCUMENTS

| 4,301,144 A | 11/1981 | Iwashita et al. |
| 4,412,989 A | 11/1983 | Iwashita et al. |
| 5,811,521 A | 9/1998 | Kluger et al. |

| 2004/0023851 A1* | 2/2004 | Barnikol ........................ 514/6 |

FOREIGN PATENT DOCUMENTS

| DE | 100 31 742 | * | 2/2002 |
| EP | 1 469 011 | * | 10/2004 |
| GB | 2 382 347 | * | 5/2003 |
| JP | 56-012308 | | 2/1981 |
| JP | 57-206622 | | 12/1982 |
| WO | WO 93/08842 | | 5/1993 |
| WO | WO 99/23065 | | 5/1999 |
| WO | WO 99/26476 | | 6/1999 |

OTHER PUBLICATIONS

Badghisi et al. Sequence Mapping of Epoxide Adducts in Human Hemoglobin with LC-Tandem MS and the Salsa Algorithm. (2002) Chem. Res. Toxicol. vol. 15, pp. 799-805.*
Isert et al. Thermolabile hemoglobin formation by 2-cyanaziridine derivatives. (1995) Toxicology Letters, vol. 78, pp. 189-194.*
Wu et al. Safety of the blood supply: role of pathogen reduction. (2003) Blood Reviews, vol. 17, pp. 111-122.*

* cited by examiner

*Primary Examiner*—Nashaat T. Nashed
*Assistant Examiner*—Holly Schnizer
(74) *Attorney, Agent, or Firm*—Sughrue Mion, PLLC

(57) ABSTRACT

The invention provides a conjugate of hemoglobin and a nucleic acid cross-linking agent.

8 Claims, No Drawings

HEMOGLOBIN CONJUGATES

This invention relates to the use of hemoglobin conjugates in the treatment of human or non-human mammalian subjects, especially to combat bacterial or viral, especially retroviral infections or to enhance the oxygen carrying capacity of the subject's blood.

It has been known to enhance the oxygen-carrying capacity of blood by administering to a mammalian subject a conjugate of hemoglobin and a polyalkylene oxide in a blood substitute. The hemoglobin-polyalkylene oxide conjugate is particularly effective since it has a longer lifetime in blood than does hemoglobin itself.

However the reaction of polyalkylene oxide with hemoglobin is inefficient since a proportion of the hemoglobin is denatured in the reaction. Moreover the affinity of the hemoglobin-polyalkylene oxide conjugate for oxygen is higher than that of hemoglobin meaning that the release of oxygen from the conjugate is hampered.

Psoralens and other fused tricyclic heterocyclic compounds have been proposed for ex vivo decontamination of blood and other materials for parenteral administration. The compounds intercalate between base pairs of nucleic acids in the material to be decontaminated and on ex vivo exposure to ultraviolet light cause the nucleic acid to become cross-linked and thus non-transcribable.

While this approach is suitable for reducing patient's risk of HIV infection on receiving a blood transfusion, it does not exercise any therapeutic effect on an infected patient, nor does it reduce a patient's risk of infection by other routes.

The present invention is based on a realisation that a conjugate of hemoglobin and psoralen or a similar nucleic acid crosslinking compound may be administered to a subject to provide both enhanced oxygen carrying capacity of blood and to combat bacterial or viral infection, e.g. retroviral infection, cancers, etc.

Thus viewed from one aspect the invention provides a conjugate of hemoglobin and a nucleic acid crosslinking agent.

Viewed from a further aspect the invention provides a pharmaceutical composition comprising a conjugate of hemoglobin and a nucleic acid cross-linking agent together with a physiologically tolerable carrier or excipient.

Viewed from a yet further aspect the invention provides a method of treatment of a human or non-human mammalian subject which method comprises parenterally administering to said subject an effective amount of a conjugate of hemoglobin and a nucleic acid cross-linking agent.

Viewed from a yet further aspect the invention provides the use of a conjugate of hemoglobin and a nucleic acid cross-linking agent for the manufacture of a medicament for parenteral administration to a human or non-human mammalian subject.

In the method of the invention, the subject is preferably also subjected to irradiation to activate the nucleic-acid cross-linking agent, for example on administration of the hemoglobin conjugate or at any time or times thereafter, e.g. up to three weeks, preferably from 2 hours up to one week, after administration. Such irradiation may be externally or internally applied and if internally applied may be by means of a radiation-emitting compound which is also administered parenterally to the patient, e.g. a fluorescent, luminescent or bioluminescent compound. In a preferred embodiment, such an emitter compound is included in the composition of the invention. Examples of such emitter compounds include luciferine. Alternatively the patient's blood may be diverted out of the body and radiation-treated, e.g. UV-irradiated, before re-entry into the body. In one preferred embodiment, the irradiation is X-ray irradiation, applied externally. This is especially suitable for treatment of AIDs patients, especially those in the final stages of their illness.

The nucleic acid crosslinking agent is preferably a psoralen, isopsoralen, acridine, haloethylamine, haloethylsulphide, epoxide or aziridine compound. Examples of such agents are disclosed for example in U.S. Pat. No. 6,194,139, U.S. Pat. No. 6,177,441 and U.S. Pat. No. 6,093,725, the contents of which are hereby incorporated by reference. Further examples are described in WO97/21346, WO96/40857, WO94/20090, WO94/03054, WO94/27433, WO95/19705, WO98/30545, WO99/26476, WO96/14739, WO95/00141, U.S. Pat. No. 6,133,460 and U.S. Pat. No. 6,017,691, the contents of which are also incorporated by reference.

Especially preferably however the nucleic acid crosslinking agent is a psoralen, more especially an 8-methoxy psoralen or a derivative thereof, particularly a carboxy($C_{1-10}$ alkyl)oxy-, carboxy($C_{1-10}$alkyl)-, carboxy($C_{1-10}$alkyl)carbonyloxy- or $C_{1-10}$alkyl carboxy-psoralen, more particularly such carboxy psoralens where the alkylene group contains 1 to 6, especially 1 to 3 carbons and particularly such carboxy psoralens where the alkylene group is linear.

The conjugation reaction may be by direct reaction of the crosslinking agent and hemoglobin or by reaction of crosslinking agent, hemoglobin and a bifunctional linking agent. Desirably the conjugate has the crosslinking agent linked to the hemoglobin via an ester, amide, ether or double ether bond, most preferably an amide bond. This may be achieved by standard synthetic chemistry technique by choosing appropriately substituted crosslinking agent and/or by use of appropriately functionalised bifunctional linking agents. The carboxy-psoralens are especially preferred as no linking agent is required. Such compounds may be prepared for example by Michael additions, by oxidation of 8-methoxy-psoralens, or by condensation of 8-methoxy psoralens or derivatives thereof with $C_{1-12}$ carboxylic acids terminally substituted with a reactive or leaving group, e.g. a halogen atom, a diazonium group or a carboxy or activated carboxy group.

8-methoxy-psoralens may be 8-carboxylated to produce the cross-linking agents for example by demethylation followed by reaction with an activated carboxy compound (e.g. an acyl halide, for example an acyl chloride) or an ester. Demethylation can be effected as described for example in Barton et al. J.C.S. Chem. 640 (1975) or J.C.S. 499 (1970), and may involve reaction with lithium iodide in boiling methylsobutylketone or aluminium carbide in nitrobenzene.

Where the crosslinking agent carries a carboxyl group suitable for reaction with a pendant amine or hydroxyl group on hemoglobin, it is especially preferred that the carboxyl group be activated before the conjugation reaction. For this purpose standard carboxyl activation techniques may be used, e.g. using a activating agent such as those routinely used in peptide synthesis (e.g. N-hydroxysuccinimide, N-hydroxy phthalimide, p-nitrophenol, pentachlorophenol, etc.) or by conversion into an acid halide group (e.g. by reaction with thionyl chloride).

The hemoglobin used for the production of the conjugates of the invention may be from any animal species having hemoglobin in its blood, especially mammalian and avian species, e.g. humans, cattle, swine, sheep, horses, dogs, monkeys, mice, rates and chickens. Particularly preferably, the hemoglobin is from the same species as the intended recipient of the conjugate. The hemoglobin may be normal or abnormal hemoglobin or a derivative thereof, e.g. a phosphate derivative (e.g. a pyridoxal-5'-phosphate or 2-nor-2-formyl pyridoxal-5'-phosphate derivative), a sulphate derivative (e.g. a pyridoxal sulfate, for example a pyridoxal-5'-sulphate, derivative), a glycerate derivative (e.g. a 2,5-diphosphoglyceric acid derivative), a sugar derivative (e.g. a derivative for a sugar with a carboxyl or phosphate group, for example glucose-6-phosphate) or an adenosine derivative (e.g. an adenosine-5'-phosphate derivative). "Abnormal" hemoglobins are discussed by Imai et al. in "Allosteric effected in hemoglobin", Cambridge University Press, 1980.

The conjugation reaction is preferably effected in a liquid phase, more preferably an aqueous phase, containing up to 25% w/v of the hemoglobin, especially 0.5 to 20% w/v, more especially 1 to 10% w/v. The reaction is preferably effected in the presence of free amines, e.g. amino acids, particularly when the hemoglobin content of the reaction mixture is above 4% w/v, as this reduces the occurrence of gelation. Desirably the crosslinking agent is used in stoichiometric or above stoichiometric quantities, e.g. the crosslinking agent and hemoglobin may be reacted in a mole ratio of 1:1 to 1:50, more preferably 1:10 to 2:10.

In the case of a reaction between the crosslinking agent and the hemoglobin in the presence of an amino acid or an amine, the molecular weight of the hemoglobin conjugate can be controlled easily. It is believed that an amino acid or amine attaches to part of the activated carboxy group of the crosslinking agent, and that the substance thus produced prevents excessive carboxyl groups from reacting with the hemoglobin. By this method, the hemoglobin conjugate of the present invention can be obtained easily without diluting the hemoglobin solution.

As an amino acid for use in the reaction, a natural amino acid, i.e. those used in protein formation, is preferably used. Examples thereof include basic amino acids such as lysine, arginine and histidine, neutral amino acids such as glycine and phenylalanine, and acidic amino acids such as glutamic acid and aspartic acid. Examples of the amines that may be used include ammonia, aliphatic amines and aromatic amines. Since the hemoglobin conjugate is to be put into the blood circulation, the substance should preferably be physiologically tolerable. A single amine or amino acid or a combination of two or more amines or amino acids can be used.

By appropriate selection of the amine or amino acid, the degree of charge on the surface of the hemoglobin conjugate, or the hydrophobic or hydrophilic nature thereof, can be adjusted as required. Thus, when the hemoglobin conjugate is to be used as a blood substitute, the interaction between the hemoglobin conjugate and red blood cells, leucocytes and blood plasma proteins which are contacted by the hemoglobin conjugate in the living body can be regulated in respect of, for example, erythrocyte sedimentation rate and immuno-recognition.

It is preferred that from 1 to 100 mole, more preferably from 5 to 20 mole, of the amino acid or amine be employed for each mole of the hemoglobin in the reaction.

The reaction mixture of the hemoglobin and the crosslinking agent preferably contains as low a content of oxygen as possible. For example, an oxygen partial pressure of 0 to 30 mmHg is preferred. For this purpose, the reaction medium is preferably degassed or flushed with an inert gas and the reaction is preferably performed under an inert gas (e.g. nitrogen, helium or argon). As regards reaction conditions other than the concentration of oxygen, all of the known art is applicable provided that the hemoglobin is not denatured.

The hemoglobin conjugate thus obtained may be freeze-dried to form a preparation for use as a drug. A stabilizing agent is preferably added to inhibit the production of methemoglobin and insoluble material. Examples of suitable stabilizing agents include monosaccharides (such as D-galactose and D-glucose) and disaccharides such as sucrose and lactose; however we have found that glucose and mannitol are especially effective.

As an example of a method of producing a freeze-dried preparation for use as a drug containing the hemoglobin conjugate, an aqueous maltose solution or maltose powder is added to an aqueous solution of the hemoglobin conjugate, and the aqueous solution thus obtained is freeze-dried by a conventional method. As regards the amount of maltose to be mixed with the hemoglobin conjugate, 0.1 to 2.0 parts by weight, preferably 0.5 to 1.2 parts by weight, of maltose is preferably employed per one part by weight of the hemoglobin conjugate. The maltose or maltose solution may for example be added to a 2 to 20 w/v % hemoglobin conjugate solution and the mixture thus obtained is frozen at −35 to −50° C. for 20 to 60 minutes and then dried under reduced pressure at 100 to 50° C. on a shelf for 5 to 70 hours to give a freeze-dried preparation for a drug. It is preferred that an amino acid such as histidine, glutamine or tryptophan be added with the maltose and/or glucose, for the preparation of the drug.

Before the freezing of the aqueous hemoglobin conjugate solution containing maltose and/or glucose, known stabilizing agents and/or salts to adjust osmotic pressure may be added.

The hemoglobin conjugate of the present invention possesses excellent properties such as the affinity of the hemoglobin for oxygen and also high stability.

Besides being produced in freeze-dried form, the compositions of the invention may be presented in other forms, e.g. powders, tablets, solutions, etc. If not in solution form, the composition is preferably dissolved in a physiologically tolerable liquid (e.g. water for injections) before administrations. Administration will typically be by injection or infusion.

Besides being administered parenterally to patients, the conjugate of the invention may be used for ex vivo treatment of blood, serum, plasma or other materials to be administered parenterally, e.g. combined with a radiation (e.g. UV) treatment of the material.

While the use of hemoglobin conjugates is the preferred form of the present invention, the invention also extends to the use of conjugates in which, in place of hemoglobin, is used a macromolecule which is capable of prolonged blood residence. In particular, in place of hemoglobin one may use proteins and glycoproteins which occur naturally in blood or on the surfaces of the cells lining the veins, arteries or capillaries (e.g. human serum albumin) or other macromolecules which can act as opsonization inhibitors, e.g. polyalkylene oxides such as polyethyleneglycol (PEG). The conjugation of such macromolecules may be effected by routine chemical methods, e.g. analogously to the production of targeted contrast agents as described for example in Torchilin "Targeted delivery of imaging agents", CRC, Boco Raton, 1995.

The invention claimed is:

1. A conjugate of hemoglobin and a nucleic acid cross-linking agent, wherein said nucleic acid cross-linking agent is selected from the group consisting of a psoralen and an isopsoralen.

2. The conjugate of claim 1, wherein said nucleic acid cross-linking agent is a psoralen.

3. The conjugate of claim 2 wherein said psoralen is an 8-methoxy psoralen.

4. The conjugate of claim 2, wherein said psoralen is meloxine.

5. A pharmaceutical composition comprising a conjugate of hemoglobin and a nucleic acid cross-linking agent together with a physiologically tolerable carrier or excipient, wherein said nucleic acid cross-linking agent is selected from the group consisting of a psoralen and an isopsoralen.

6. The composition of claim 5, wherein said nucleic acid cross-linking agent is a psoralen.

7. The composition of claim 5 wherein said conjugate is a conjugate of hemoglobin and an 8-methoxy psoralen.

8. The composition of claim 5 wherein said conjugate is a conjugate of meloxine and hemoglobin.

* * * * *